(12) United States Patent
Bouliane (10) Patent No.: US 8,932,303 B2
(45) Date of Patent: Jan. 13, 2015

(54) SURGICAL SCREWDRIVER

(75) Inventor: Martin Bouliane, Carlsbad, CA (US)

(73) Assignee: Alphatec Spine Inc, Carlsbad, CA (US)

( * ) Notice: Subject to any disclaimer, the term of this patent is extended or adjusted under 35 U.S.C. 154(b) by 276 days.

(21) Appl. No.: 13/453,622

(22) Filed: Apr. 23, 2012

(65) Prior Publication Data

US 2013/0282019 A1 Oct. 24, 2013

(51) Int. Cl.
*A61B 17/58* (2006.01)
*A61B 17/60* (2006.01)
*A61F 2/00* (2006.01)

(52) U.S. Cl.
USPC ....................................................... 606/104

(58) Field of Classification Search
CPC ........... A61B 17/8891; A61B 17/8888; A61B 17/8886; A61B 17/8883; A61B 17/888; A61B 17/8877; A61B 17/7082
USPC ................................................. 606/86 A, 104
See application file for complete search history.

(56) References Cited

U.S. PATENT DOCUMENTS

| | | | | |
|---|---|---|---|---|
| 5,573,530 A * | 11/1996 | Fleury et al. | ....................... | 606/1 |
| 8,460,307 B2 * | 6/2013 | Saidha et al. | ................. | 606/104 |
| 8,777,960 B2 * | 7/2014 | Murray et al. | ................ | 606/104 |
| 8,808,307 B2 * | 8/2014 | Robinson | ....................... | 606/104 |
| 2008/0221583 A1 * | 9/2008 | Sharifi-Mehr et al. | ......... | 606/104 |
| 2009/0326545 A1 * | 12/2009 | Schaffhausen | ................. | 606/104 |
| 2011/0306984 A1 * | 12/2011 | Sasing | ............................ | 606/104 |
| 2012/0253402 A1 * | 10/2012 | McLean | ......................... | 606/264 |
| 2013/0150864 A1 * | 6/2013 | Marik et al. | ................... | 606/104 |

* cited by examiner

*Primary Examiner* — David Bates
(74) *Attorney, Agent, or Firm* — Michael J. Loi (57) ABSTRACT

An instrument for attachment and insertion of a screw assembly into a surgical site includes a housing, an attachment shaft, and a drive shaft. The housing including a movable hub. The attachment shaft includes a proximal end for coupling to the housing and a distal end with a flexible portion for selectively attaching to a receiver of the screw assembly. The drive shaft within the attachment shaft includes a proximal end for selectively engaging the hub and a distal end with a driving feature for driving a head of the screw assembly.

14 Claims, 8 Drawing Sheets

SURGICAL SCREWDRIVER

FIELD

The present disclosure generally relates to the field of spinal orthopedics, and more particularly to instruments for inserting surgical screws.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature.

Generally the correct curvature is obtained by manipulating the vertebrae into their proper position and securing that position with a rigid system of screws and rods. Often, prior to inserting a screw, a bore may be drilled and tapped to receive the screw. The screws may be inserted into the pedicles of the vertebrae to act as bone anchors, and the rods may be inserted into heads of the screws. Two rods may run substantially parallel to the spine and secure the spine in the desired shape and curvature. Thus the rods, which are shaped to mimic the correct spinal curvature, force the spine into proper alignment. Bone grafts are then placed between the vertebrae and aid in fusion of the individual vertebrae together to form a correctly aligned spine.

A surgical screwdriver may be used to insert a screw into the vertebra. The screwdriver typically includes a driving end with a driving feature and a handle portion for applying torque to the screw. The driving feature typically includes a geometry corresponding to a recess or receiving feature of the screw. The driving feature may frictionally or compressively engage the screw to temporarily attach to the screwdriver during insertion into the vertebrae. In some cases, a threaded section of the screwdriver may be used to engage with the heads on the screws. For example, the driving feature may be aligned with the receiving feature of the screw and the threaded section may be threaded onto the mating threads in the head of the screws.

During a surgical procedure, a surgeon, assistant, or nurse may need to attach numerous screws to screwdrivers prior to insertion into a surgical area. In some cases, the driving feature may not provide sufficient friction forces or compressive forces to hold the screw in place as the screwdriver is transferred to the surgeon during the surgical procedure. Screws may fall off of the screwdriver causing delays and risk of contamination. In other cases, the screwdriver may be difficult to align with the screw and head. The driving feature may need to be aligned with the receiving feature prior to threading the threaded section onto the mating threads of the head. Therefore, a screwdriver that provides secure, quick, and reliable attachment of the screw is needed.

SUMMARY

An instrument for attachment and insertion of a screw assembly into a surgical site includes a housing, an attachment shaft, and a drive shaft. The housing including a movable hub. The attachment shaft includes a proximal end for coupling to the housing and a distal end with a flexible portion for selectively attaching to a receiver of the screw assembly. The drive shaft within the attachment shaft includes a proximal end for selectively engaging the hub and a distal end with a driving feature for driving a head of the screw assembly.

In other features, the flexible portion elastically deforms to attach to the receiver of the screw assembly. The flexible portion includes a first thread for engaging a second thread of the receiver of the screw assembly. The attachment shaft rotates to advance the first thread relative to the second thread and detach the flexible portion from the receiver of the screw assembly. The drive shaft translates within the attachment shaft to engage the hub. The housing includes a first configuration that positions the hub towards the proximal end of the drive shaft and a second configuration that positions the hub away from the proximal end of the drive shaft. A bias mechanism biases the proximal end of the drive shaft away from the hub.

An instrument that attaches to and drives a screw assembly into a surgical site includes a housing, a first shaft, and a second shaft. The housing includes a first portion with a hub and a second portion. The first shaft includes a proximal end that couples with the second portion, a distal end with a flexible portion for selectively attaching to a receiver of the screw assembly, and a cannula extending from the proximal end to the distal end. The second shaft includes a proximal end with an engagement feature configured to selectively engage the hub and a distal end with a driving feature for driving a head of the screw assembly.

In other features, a bias mechanism biases the engagement feature away from the hub. The distal end of the first shaft includes one or more slots that form the flexible portion. The distal end of the second shaft includes a recessed portion. The housing includes a first configuration that engages the hub with the engagement feature and a second configuration that disengages the hub from the engagement feature. The flexible portion includes elastically deforms from a first configuration to a second configuration as the first shaft advances within the receiver of the screw assembly. The flexible portion elastically deforms from the second configuration to the first configuration to threadably engage the first shaft with the receiver of the screw assembly. The first shaft rotates to disengage from the receiver of the screw assembly.

DETAILED DESCRIPTION

Accordingly, an instrument for insertion of surgical screws according to the principles of the present disclosure includes features for secure, quick, and reliable attachment of a screw for insertion into a surgical area. The instrument includes a flexible portion at its distal end that deflects to engage with a head of the screw. The flexible portion elastically deflects as the distal end advances into the head of the screw. The flexible portion elastically returns or straightens to attach to the head of the screw. The instrument includes a driving feature at its distal end that may couple and decouple with an actuating portion of the instrument.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1:
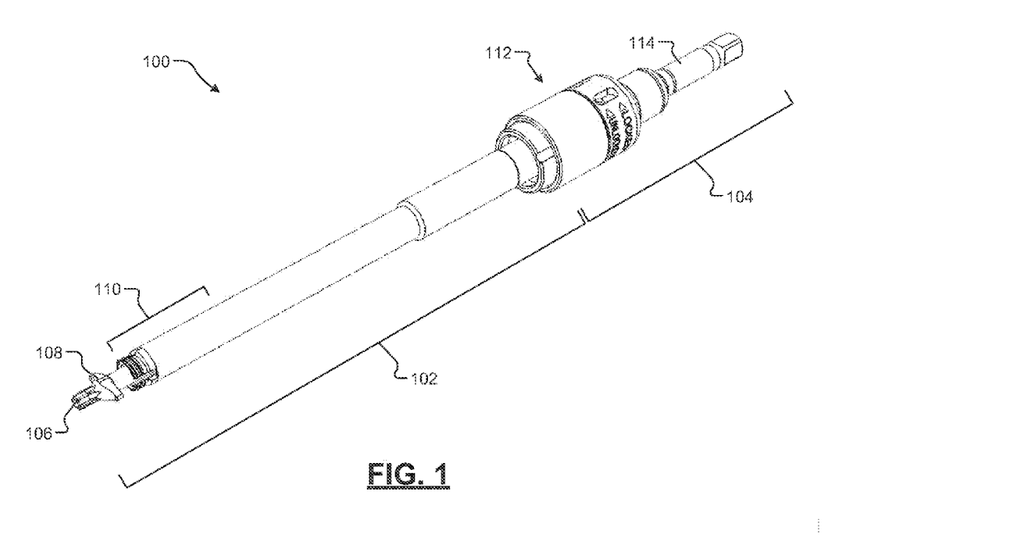
FIG. 1 is a perspective view of an exemplary instrument for insertion of surgical screws according to the principles of the present disclosure.

Referring now to FIG. 1, an exemplary instrument 100 for insertion of a surgical screw includes features for secure, quick, and reliable attachment of a screw assembly and insertion into a surgical site. The instrument 100 includes a distal portion 102 and a proximal portion 104. The distal portion 102 may include a driving feature 106 for engagement with the screw assembly. The distal portion 102 may include an alignment feature 108 for alignment with the screw assembly. The distal portion 102 may include an attachment feature 110 for attachment with the screw assembly. The proximal portion 104 may include a housing 112 and an actuator 114. The actuator 114 may selectively couple and decouple from the driving feature 106. The housing 112 encloses additional features for selective engagement and disengagement of the driving feature 106 and the actuator 114. The housing 112 may include a ratcheting system. A handle (not shown) may selectively couple with the actuator 114 for gripping and applying torque to the instrument 100. The handle may include the ratcheting system.

Figure 2:
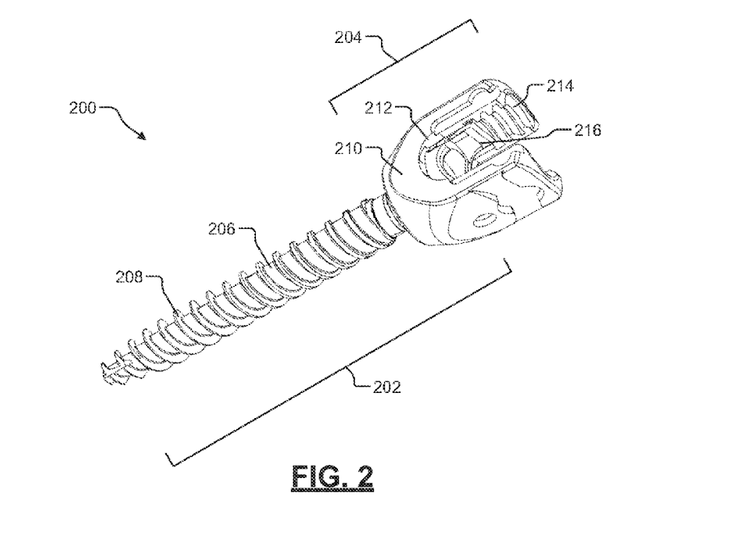
FIG. 2 is a perspective view of an exemplary surgical screw for use with the instrument of FIG. 1.

FIG. 2 illustrates an exemplary screw assembly 200 for use with the instrument 100 in a surgical procedure. Other examples of screw assemblies may be found in U.S. Pub. No. 2009/0171391 and 2010/0036443 which are incorporated herein by reference. In FIG. 2, the screw assembly 200 includes a screw 202 and a receiver 204. The screw 202 may be inserted into the receiver 204. For example, the screw assembly 200 may include a polyaxial screw assembly in which the receiver 204 may pivot and rotate about a spherical head on a proximal end of the screw 202. The screw 202 includes a shank 206 extending distally from the spherical head. The shank 206 may include a thread 208 for attachment to bone such as a vertebra. The spherical head may include a recess (not shown) configured to receive the driving feature 106 of the instrument 100.

Although the present disclosure may refer to a polyaxial screw assembly, any screw assembly including a receiver 204 as described herein may be used in conjunction with the instrument 100. The receiver 204 may include a body 210, commonly referred to as a "tulip", that forms a U-shaped channel 212 for receiving a fixation rod (not shown). A setscrew (also not shown) may be used to secure the fixation rod within the channel 212. For example, the body 210 may include an internal female thread 214 at a proximal end for receiving the setscrew. The screw assembly 200 may further include a bushing 216 disposed between the screw 202 and the receiver 204.

Figure 3A:
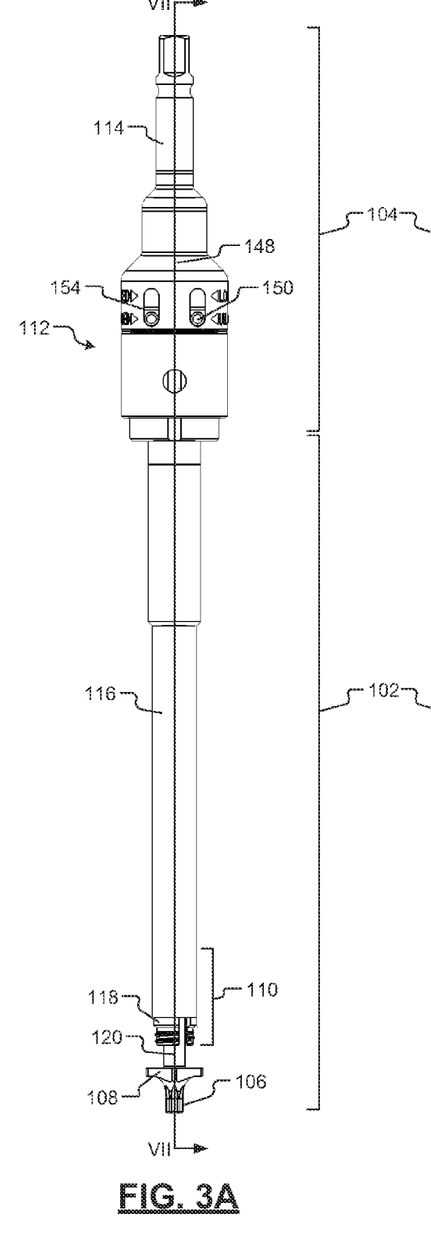
FIGS. 3A and 3B are side views of the instrument of FIG. 1 according to the principles of the present disclosure.
Figure 3B:
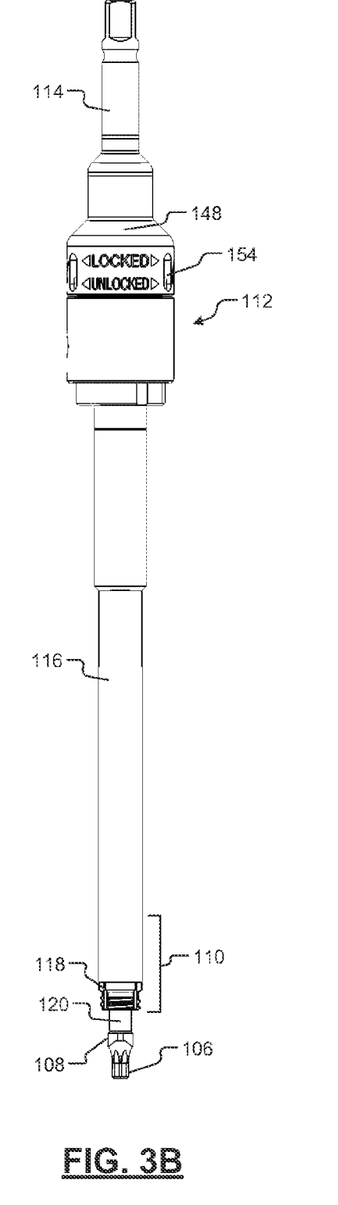
Figure 4:
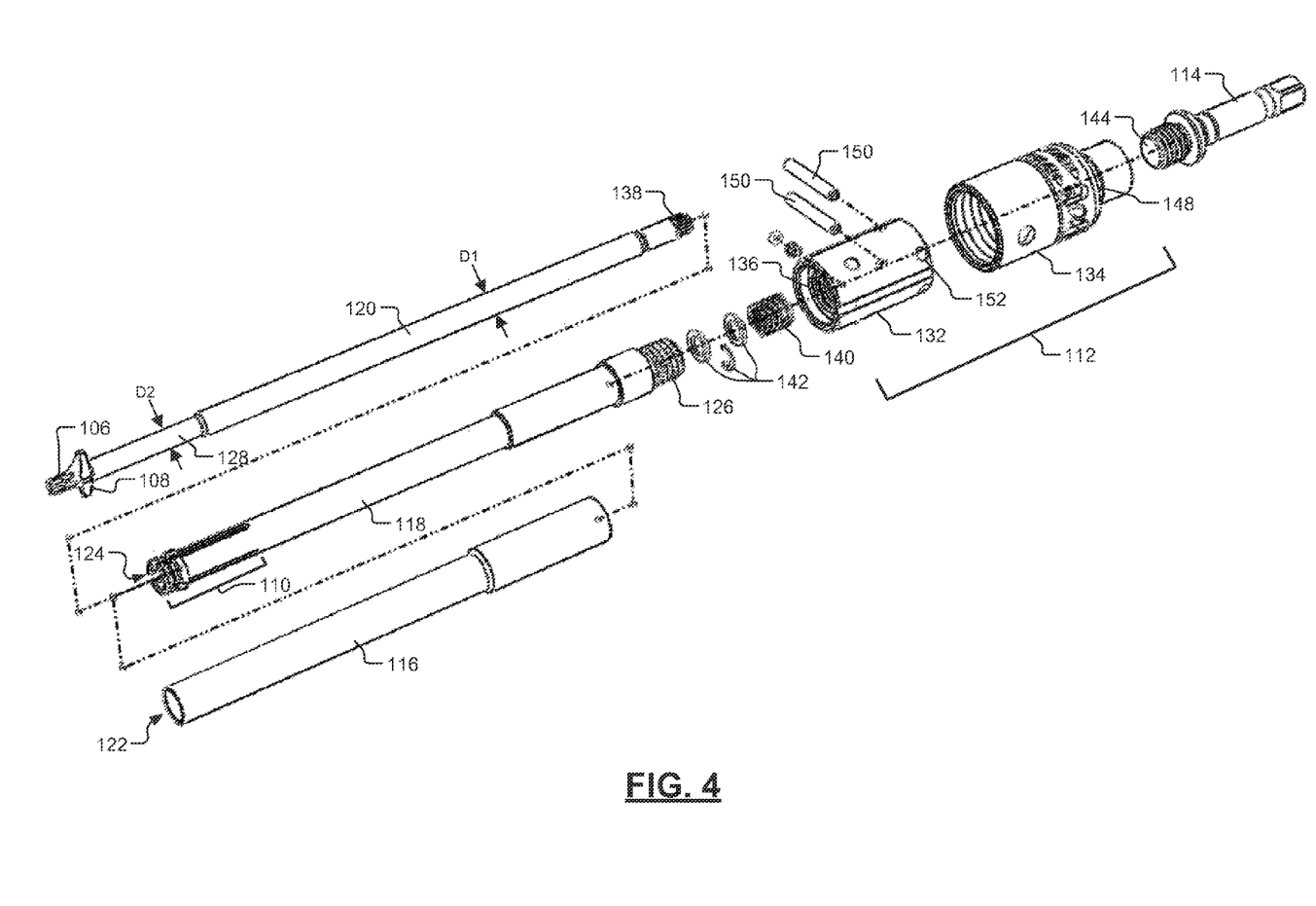
FIG. 4 is an exploded perspective view of the instrument of FIG. 1 according to the principles of the present disclosure.

Referring now to FIG. 3A-4, side views and exploded views of the instrument 100 illustrate additional features of the distal portion 102 and the proximal portion 104. The distal portion 102 may include one or more concentric shafts. For example, the instrument 100 may include an outer shell 116, a first shaft 118, and a second shaft 120. The outer shell 116 may include a hollow portion 122 extending from its proximal end to its distal end for receiving the first shaft 118. The outer shell 116 may provide structural support to the distal portion 102 to prevent flexing of the first shaft 118 and/or the second shaft 120. The outer shell 116 may include a substantially smooth surface within the hollow portion 122 and slide relative to the first shaft 118. The outer shell 116 may be described as a guide shell that guides the first and second shafts 118 and 120 when inserting a screw assembly 200 at a surgical site.

The first shaft 118 may include a cannula 124 for receiving the second shaft 120. The first shaft 118 may include the attachment feature 110 on its distal end for attachment to the screw assembly 200 as described herein. The attachment feature 110 may include elastic and or flexible members that bend radially inward towards the second shaft 120 as described below. The first shaft 118 may include a substantially smooth surface within the cannula 124. A threaded portion 126 at a proximal end of the first shaft 118 attaches to the housing 112. The first shaft 118 may be described as an attachment shaft that attaches to the receiver 204 of the screw assembly 200.

The second shaft 120 may include the driving feature 106 and the alignment feature 108 on its distal end. The distal end may include a recessed portion 128 that permits the attachment feature 110 to bend radially inward without interfering with the second shaft 120. For example, the recessed portion 128 may include a smaller diameter than the proximal end of the second shaft 120. The second shaft 120 may include a first diameter D1 at its proximal end and a second diameter D2 less than the first diameter D1 at its distal end. The second shaft 120 may include a substantially smooth outer surface for sliding engagement within the cannula 124. A proximal end of the second shaft 120 may selectively couple with the housing 112 and/or actuator 114 as described herein. The second shaft 120 may be described as a drive shaft that drives the screw 202 of the screw assembly 200 into the bone.

The proximal portion 104 may include the housing 112 and the actuator 114. In some examples, the housing 112 may include two portions such as a first portion and a second portion. The first portion may include an inner portion 132 and the second portion may include an outer portion 134 as illustrated in the present example in FIG. 3. The inner portion 132 may translate and/or rotate within the outer portion 134 to engage with one or more of the first and second shafts 118 and 120. A distal end of the inner portion 132 may receive the first shaft 118. For example, internal threads 136 within the distal end of the inner portion 132 may receive the proximal threaded portion 126 of the first shaft 118. The first shaft 118 may thread onto the inner portion 132.

Within the inner portion 132, a proximal end of the second shaft 120 may extend through a proximal opening of the cannula 124 of the first shaft 118. The proximal end of the second shaft 120 may include an engagement feature 138 configured to selectively engage and disengage with a mating feature within the housing 112. For example, the engagement feature 138 may include a splined, toothed, or ridged surface. A bias member 140 within the housing 112 may bias the second shaft 120 distally away from the housing 112. For example, the bias member 140 may include a coil spring that engages the proximal end of the second shaft 120. One or more clips 142 may couple to the second shaft 120 to engage the bias member 140. A proximal end of the bias member 140 may engage an inner surface of the inner portion 132 of the housing 112. A distal end of the bias member 140 may engage the clips 142. Alternately, a raised portion or projections extending radially from the second shaft 120 may engage the bias member 140.

The outer portion 134 may slide over the inner portion 132 to position the actuator 114 into engagement with the drive shaft 120. For example, the actuator 114 may rotatably couple within a proximal end of the outer portion 134. The actuator 114 may rotate freely within the proximal end of the outer portion 134. The actuator 114 may include a thread 144 that engages another mating thread 146 of the outer portion 134 as more clearly seen in FIGS. 7A-7C. At a distal end of the actuator 114 or a proximal end of the outer portion 134, a hub 148 may include ridges, teeth, and/or splines that mate with the keyed portion 138 of the third shaft 130. One or more guide pins 150 may couple the inner portion 132 with the outer portion 134. The guide pins 150 may maintain alignment between the inner portion 132 and the outer portion 134. For example, the guide pins 150 may extend through apertures 152 of the inner portion 132 and into slots 154 of the outer portion 134. The guide pins 150 may restrict movement of the outer portion 134 about the inner portion 132 to translation proximally and distally. The guide pins 150 may transfer force from the actuator 114 and outer portion 134 to the inner portion 132 to rotate the second shaft 118.

FIGS. 5A-5D illustrate features of the distal end of the first shaft 118 for engagement and disengagement of the receiver portion 204 of the screw assembly 200 of FIG. 2. The first shaft 118 may include the attachment feature 110. The attachment feature 110 may include one or more flexible portions 156 for a quick, snap-fit attachment of the receiver portion 204. The flexible portions 156 may be formed by one or more slots 158 in the distal end of the first shaft 118. The slots 158 may extend from a distal opening 160 of the cannula 124 and along a length of the first shaft 118. The slots 158 may communicate with the distal opening 160. An external male thread 162 on the distal end of the attachment feature 110 may mate with the internal female thread 214 of the receiver 204 as shown in FIG. 2. The external thread 162 may include a tapered distal surface.

Figure 5A:
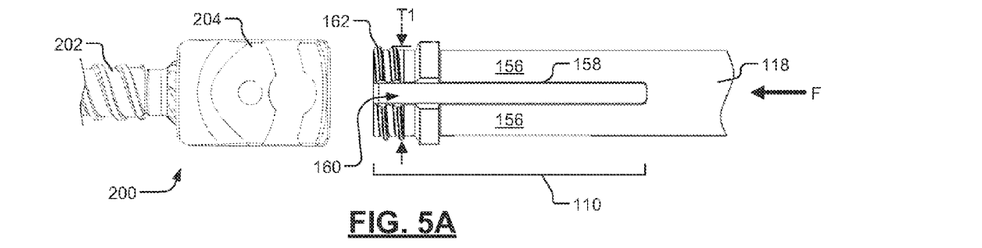
FIGS. 5A-5D are side views illustrating attachment and detachment of a portion of the instrument with a screw assembly according to the principles of the present disclosure.
Figures 5B, 5C:
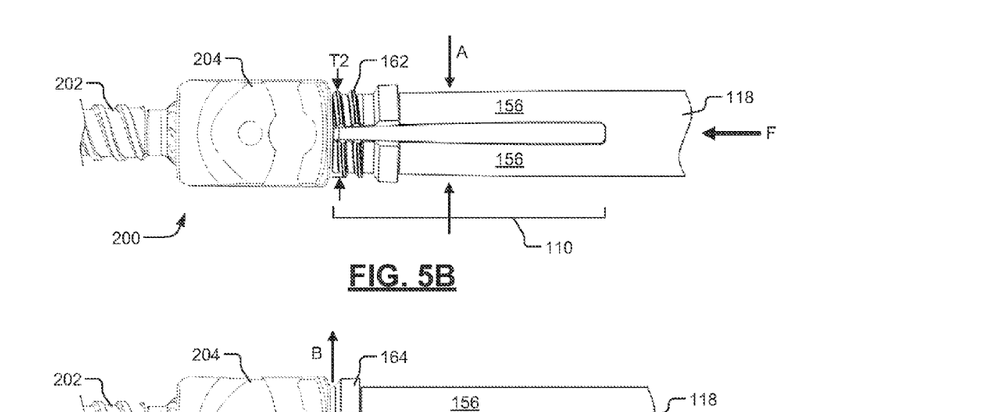

The flexible portions 156 enable the first shaft 118 to elastically bend from a first configuration shown in FIG. 5A to a second configuration shown in FIG. 5B. In the first configuration, the flexible portions 156 may be substantially parallel with the rest of the first shaft 118. The external thread 162 may include a first diameter T1 sufficient for threaded engagement with the internal thread 214 of the receiver 204. For example, the first diameter T1 may include a major or outside diameter of the external thread 162. The first diameter may be greater than a minor or inside diameter of the internal thread 214. In the second configuration shown in FIG. 5B, the flexible portions 156 deflect radially inward as indicated by arrows A from the rest of the first shaft 118. The external thread 156 may decrease to a second diameter T2 less than the first diameter T1 for sliding engagement over the internal thread 214. For example, the second diameter T2 may be less than the minor diameter or inside diameter of the internal thread 214.

In operation, the instrument 100 may be attached to the screw 200 by inserting the first shaft 118 into the receiver 204 by applying a force F on the first shaft 118 as shown in FIG. 5A. The force F may be applied on proximal portion 102 of the instrument 100 and transferred through the housing 112 to the first shaft 118. As the first shaft 118 encounters the receiver 204, the internal thread 214 interferes with passage of the external thread 162 due to the external or major diameter including the first diameter T1 of the first configuration. As shown in FIG. 5B, increasing the force F causes the flexible portions 156 to deflect radially inward until the external diameter reaches the second diameter T2 of the second configuration. The first shaft 118 may continue to advance into the receiver 204 until the external thread 162 mates with the internal thread 214. In other examples, the flexible portions 162 may include a stop 164 that limits advancement of the first shaft 118 distally.

Figure 5D:
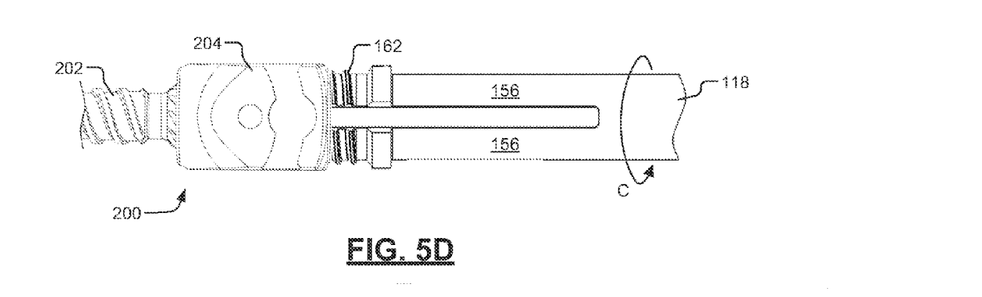

Once the external thread 162 and the internal thread 214 are in threaded engagement, the flexible portions 156 may deflect radially outward as indicated by arrows B until the external diameter returns to the first diameter of the first configuration as shown in FIG. 5C. To remove the instrument 100 from the screw 200, the first shaft 118 may be rotated to advance the external thread 162 relative to the internal thread 214 as shown in FIG. 5D. Thus, the first shaft 118 may be unthreaded to remove the instrument 100 from the screw assembly 200 by rotation as indicated, for example, by arrow C.

Figure 6A:
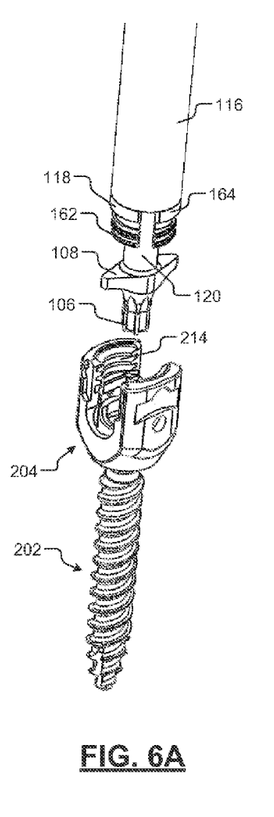
FIGS. 6A-6C are perspective views illustrating attachment of the instrument to the screw assembly according to the principles of the present disclosure.
Figure 6B:
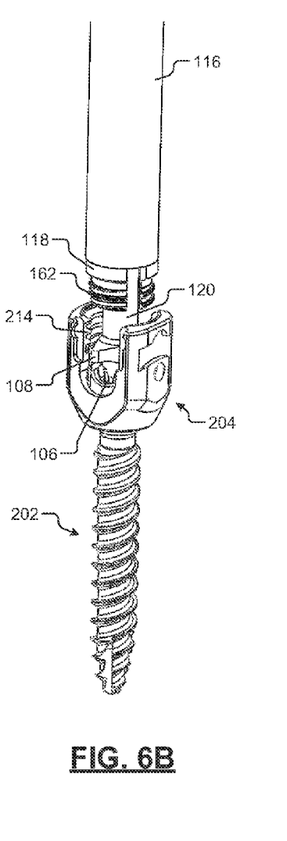
Figure 6C:
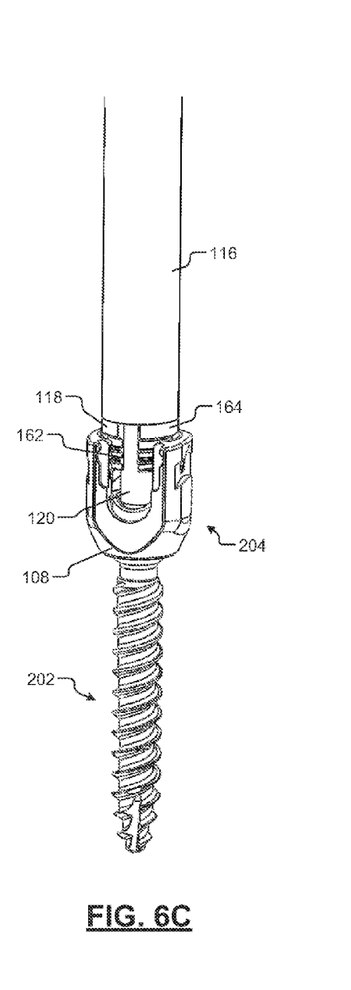

FIGS. 6A-6C illustrate insertion of the instrument 100 into the screw 200 according to the principles of the present disclosure. In FIG. 6A, the second shaft 120 extends the driving feature 106 away from the flexible portions 156. As the driving feature 106 approaches the receiver 204 of the screw 200, the flexible portions 156 are in the first configuration. In FIG. 6B, the driving feature 106 begins to engage the screw 202 as the external thread 162 on the flexible portions 156 approaches the receiver 204. The second shaft 120 may translate proximally relative to the first shaft 118 as the driving feature 106 engages the recess (not shown). The flexible portions 156 may continue to advance into the receiver 204 as described above with reference to FIGS. 5A-5D. In FIG. 6C, the external thread 162 is in threaded engagement with the internal thread 214 of the receiver 204. The flexible portions 156 have deflected radially outward. The stop 164 may limit advancement of the instrument 100.

Figure 7A:
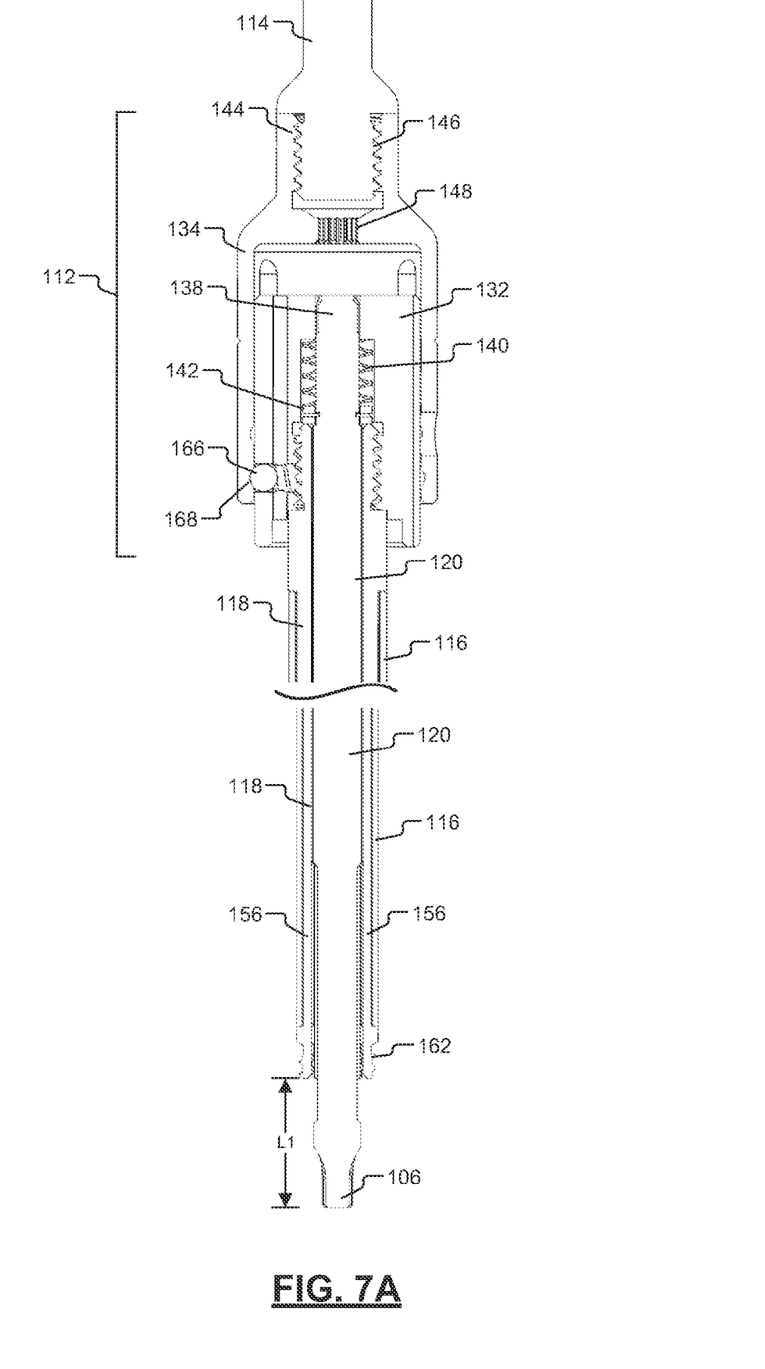
FIGS. 7A-7C are cross-sectional views of the instrument along a plane VII of FIG. 3A illustrating the instrument in various configurations according to the principles of the present disclosure.
Figure 7B:
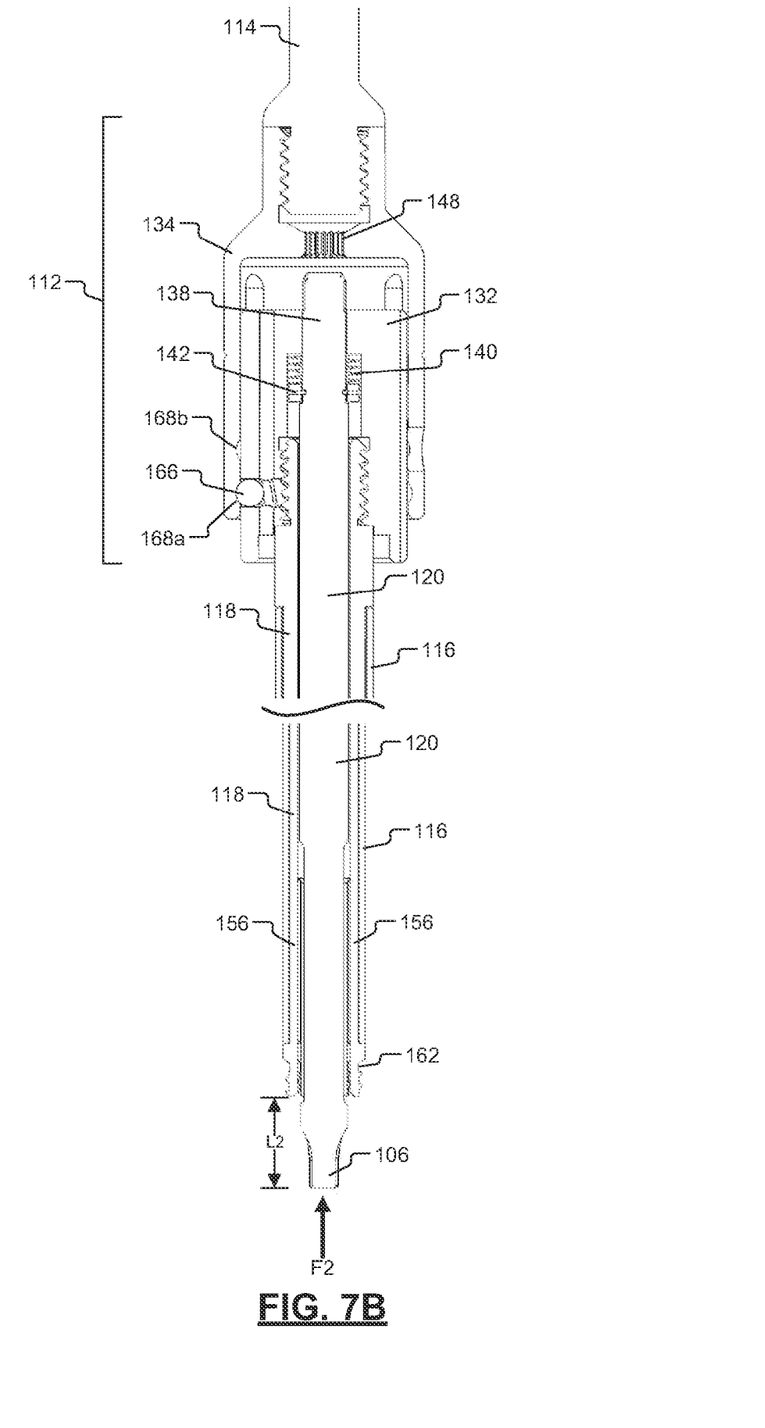
Figure 7C:
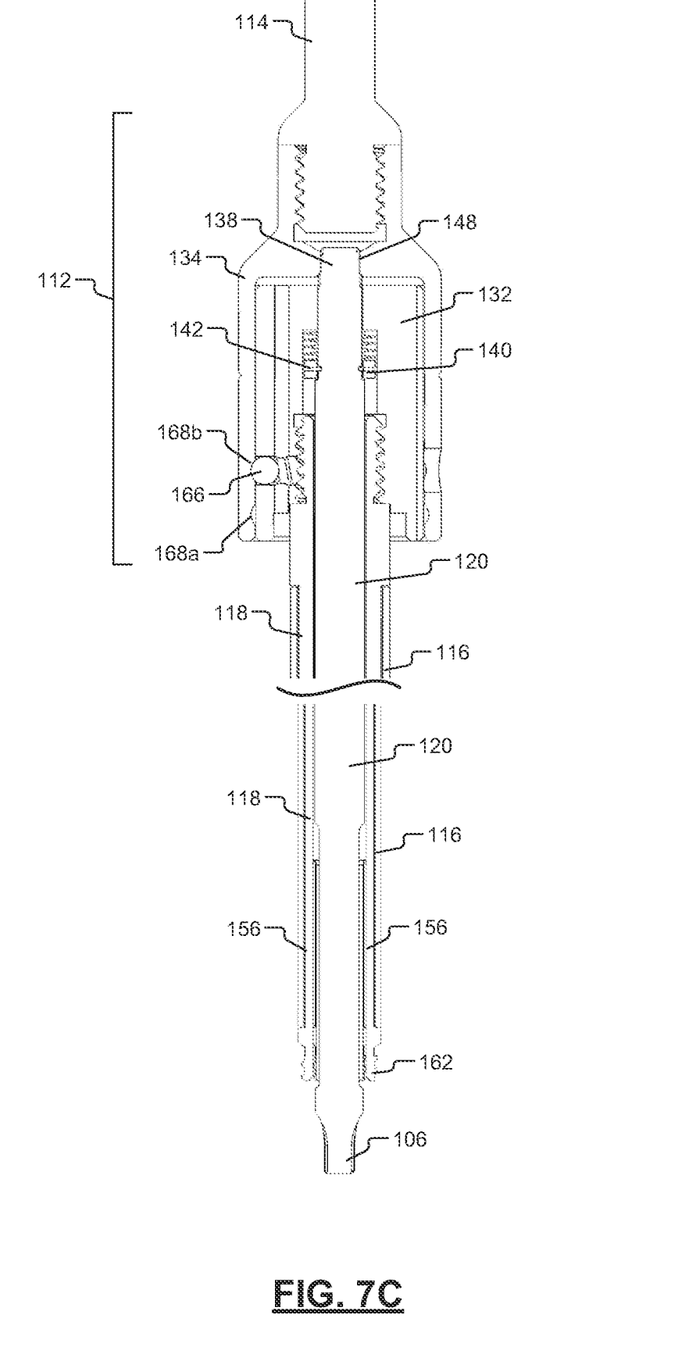

Referring now to FIGS. 7A-7C, cross-sectional views illustrate additional features for actuation of the instrument 100 when attaching to and driving the screw assembly 200. FIG. 7A illustrates the instrument 100 as it may appear when unattached to the screw assembly 200 and may be referred to as an unattached configuration. In the unattached configuration, the instrument 100 may be in condition to be inserted into the receiver 204 of the screw assembly 200 as illustrated in FIGS. 5A-5B and 6A-6B. FIG. 7B illustrates the instrument 100 as it may appear with the flexible portions 156 attached to the receiver 204 of the screw assembly 200 and the driving feature 106 engaging the head of the screw 202 and may be referred to as an attached configuration. In the attached configuration, the instrument 100 may be used to position an attached screw assembly 200 within the surgical site or rotated to be removed from the screw assembly 200 as illustrated in FIGS. 5C-5D and 6C. FIG. 7C illustrates the instrument 100 as it may appear in the attached configuration but additionally with the hub 148 engaged with the engagement feature 138 for a driving configuration. In the driving configuration, the instrument 100 may be used to drive the screw assembly 200 into bone at the surgical site.

Referring back to FIG. 7A, the flexible portions 156 of the instrument 100 are in the first configuration prior to insertion into the receiver 204 of the screw assembly 200 and corresponding to FIGS. 5A and 6A. The bias member 140 biases the second shaft 120 distally to an extended position. For example, the bias member 140 may be disposed between the clips 142 and the inner portion 132 of the housing 112. The bias member 140 may apply force to the clip 142 that positions the second shaft 120 in the extended position. The driving feature 106 on the distal end of the second shaft 120 may extend away from the distal end of the flexible portions 156 a first length L1. The hub 148 within the housing 112 is disengaged from the engagement feature 138 on the proximal end of the second shaft 120. For example, the outer portion 134 of the housing 112 may be positioned proximally from the inner portion 132 of the housing 112. A retaining mechanism, such as a ball 166 and detents 168, may retain the outer portion 134 relative to the inner portion 132. For example, in FIGS. 7A and 7B, the ball 166 engages a first detent 168a in an unlocked position. In the unlocked position, the housing 112, actuator 114, outer shell 116, and first shaft 118 may rotate freely about the second shaft 120. The ball 166 may engage with a first detent 168a.

In FIG. 7B, a force F2 applied to the driving feature 106 translates the second shaft 120 proximally into the housing 112. The force F2 may be due to insertion of the instrument 100 into the screw assembly 200. For example, as the driving feature 106 engages the head of the screw 202, the second shaft 120 may be forced proximally relative to the first shaft 118. The proximal end of the second shaft 120 including the engagement feature 138 likewise translates proximally towards the hub 148. The engagement feature 138 may not yet engage the hub 148. The ball 166 and detent 168a maintain the outer portion 134 and inner portion 132 in the unlocked position thus enabling the external thread 162 to be backed out of the receiver 204 as shown in FIG. 5D. At the distal end of the instrument 100, the external thread 162 on the flexible portions 156 may engage the internal thread 214 of the receiver 204 (not shown). The bias member 140 applies a counterforce on the second shaft 120 forcing the driving feature 106 into engagement with the recess in the head of the screw 202 (also not shown). Engagement of the external thread 162 and the internal thread 214 retain the receiver 204. The driving feature 106 may extend away from the distal end of the flexible portions 156 at a second length L2 that is less than the first length L1.

In FIG. 7C, the outer portion 134 of the housing 112 advances distally over the inner portion 132 to engage the hub 148 with the engagement feature 138 of the second shaft 120. The ball 166 may move from the first detent 168a to a second detent 168b to retain the outer portion 134 relative to the inner portion 132 in a locked position. With the hub 148 and engagement feature 138 engaged, rotation of the actuator 114 causes rotation of the second shaft 120 and thus, rotation of the driving feature 106. The driving feature 106 may drive the screw assembly 200 into the bone.

To remove the instrument 100 once the screw assembly 200 has been attached to the bone, the steps for attachment may be reversed. For example, the outer portion 134 may be advanced proximally over the inner portion 132 to disengage the hub 148 from the engagement feature 138 of the second shaft. The retention mechanism 166 may retain the outer portion 134 relative to the inner portion 132 in the unlocked position. With the hub 148 and engagement feature 138 disengaged, rotation of the actuator 114 causes rotation of the first shaft 118 and thus, rotation of the external thread 162. The external thread 162 may be backed out from the receiver 204. The bias member 140 may force the driving feature 106 to the extended position as well.

Although the present example includes a two-part housing 112 with inner portion 132 and outer portion 134, one skilled in the art may appreciate that elements of the inner portion 132 and the outer portion 134 may be interchangeable. For example, the instrument 100 may include an outer portion that couples with the first shaft 118 and an inner portion that couples with the actuator 114. The second shaft 120 may extend through the first shaft 118 into the outer portion and the inner portion may advance distally to engage the hub 148 with the second shaft 120.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. An instrument for attachment and insertion of a screw assembly into a surgical site, comprising:
   a housing including a movable hub rotatable relative to the housing;
   an attachment shaft that includes a proximal end for coupling to the housing around the hub and a distal end with a resiliently flexible portion for selectively attaching to a receiver of the screw assembly; and
   a drive shaft configured to pass within the attachment shaft that includes a proximal end for selectively engaging the hub and a distal end with a driving feature for driving a head of the screw assembly;
   wherein the flexible portion includes a first thread for engaging a second thread of the receiver of the screw assembly, wherein in a first expanded configuration, the first thread is capable of threaded interaction with the second thread; and wherein in a second configuration the first thread is capable of sliding over the second threads to be inserted into the second threads.

2. The instrument of claim 1, wherein the flexible portion is configured to elastically deform into the first configuration to permit attachment of the first threads to the second threads of the receiver of the screw assembly.

3. The instrument of claim 1, wherein the attachment shaft is configured to rotate relative to the receiver to advance the first thread relative to the second thread and detach the flexible portion from the receiver of the screw assembly.

4. The instrument of claim 1, wherein the drive shaft is configured to translate within the attachment shaft to engage the hub.

5. The instrument of claim 1, wherein the housing includes a housing first configuration that positions the hub towards the proximal end of the drive shaft such that rotation of the housing causes rotation of the drive shaft and a housing second configuration that positions the hub away from the proximal end of the drive shaft such that rotation of the housing causes rotation of the attachment shaft.

6. The instrument of claim 1, further comprising a bias mechanism located between the proximal end of the drive shaft and the housing that biases the proximal end of the drive shaft away from the hub.

7. An instrument that attaches to and drives a screw assembly into a surgical site, comprising:
 a housing including a first portion with a hub and a second portion;
 a first shaft including a proximal end that couples with the second portion, a distal end with a flexible portion for selectively attaching to a receiver of the screw assembly, and a through hole extending from the proximal end to the distal end; and
 a second shaft including a proximal end with an engagement feature configured to selectively engage the hub and a distal end with a driving feature for driving a head of the screw assembly,
 wherein the flexible portion elastically deforms from a first expanded configuration to a second configuration as the first shaft advances in the distal direction within the receiver of the screw assembly,
 wherein in the second configuration, the flexible portion is capable of sliding over a thread within the receiver of the screw assembly, and
 wherein the flexible portion elastically deforms from the second configuration to the first expanded configuration to threadably engage the first shaft with the thread of the receiver of the screw assembly.

8. The instrument of claim 7, further comprising a bias mechanism located between the proximal end of the second shaft and the housing second portion that biases the engagement feature away from the hub.

9. The instrument of claim 7, wherein the distal end of the first shaft includes one or more slots in the flexible portion.

10. The instrument of claim 7, wherein the distal end of the second shaft includes a recessed portion located proximate the driving feature.

11. The instrument of claim 7, wherein the housing and second shaft include a first housing configuration that engages the hub with the engagement feature and a second housing configuration that disengages the hub from the engagement feature.

12. The instrument of claim 7, wherein the first shaft is configured to rotate relative to the receiver to disengage the first shaft from the receiver of the screw assembly.

13. The instrument of claim 7, wherein the flexible portion is configured to elastically deform by deflecting radially inward from the first expanded configuration to the second configuration.

14. The instrument of claim 7, wherein the flexible portion is configured to elastically deform by deflecting radially outward from the second configuration to the first expanded configuration.

* * * * *